United States Patent [19]

Heinzelman et al.

[11] Patent Number: 5,456,664
[45] Date of Patent: Oct. 10, 1995

[54] CATHETER STEERING MECHANISM

[75] Inventors: Bert D. Heinzelman, Tenafly, N.J.; Christopher J. Brooks, Glen Head, N.Y.

[73] Assignee: EP Technologies, Inc., Sunnyvale, Calif.

[21] Appl. No.: 339,451

[22] Filed: Nov. 14, 1994

Related U.S. Application Data

[63] Continuation of Ser. No. 976,693, Nov. 13, 1992, Pat. No. 5,364,351.
[51] Int. Cl.⁶ ................................................. A61M 37/00
[52] U.S. Cl. ............................................. 604/95; 128/772
[58] Field of Search .......................... 604/95, 280, 282, 604/159; 128/656–658, 772

[56] References Cited

U.S. PATENT DOCUMENTS

| | | | |
|---|---|---|---|
| 5,185,004 | 2/1993 | Lashinski | 604/95 |
| 5,199,950 | 4/1993 | Schmitt et al. | 604/95 |
| 5,254,088 | 10/1993 | Lundquist et al. | 128/772 X |
| 5,273,535 | 12/1993 | Edwards et al. | 604/95 |
| 5,395,329 | 3/1995 | Fleischhacker et al. | 604/95 |

*Primary Examiner*—John D. Yasko
*Attorney, Agent, or Firm*—Ryan, Maki & Hohenfeldt

[57] ABSTRACT

The invention provides an improved catheter steering mechanism for pulling a first catheter steering wire while simultaneously allowing a second catheter steering wire to remain static, and vice versa. The mechanism includes at least one rotatable gear and means, such as a rotatable knob, for manually rotating the gear. A first linearly slidable toothed rack is attached to the proximal end of one steering wire, and a second linearly slidable toothed rack is attached to the proximal end of the other steering wire. A toothed gear rotatable by rotation of the knob engages each of the toothed racks to move them linearly in opposite directions in response to rotation of said gear. Preferably three intermeshing gears are used so that movements of the racks are in the same direction as the rotation of the knob. Preferably the steering wires are connected to the racks by connections that transfer tension as the racks move away from the wires but allow the wires to remain static, when the rack moves toward its associated wire.

6 Claims, 2 Drawing Sheets

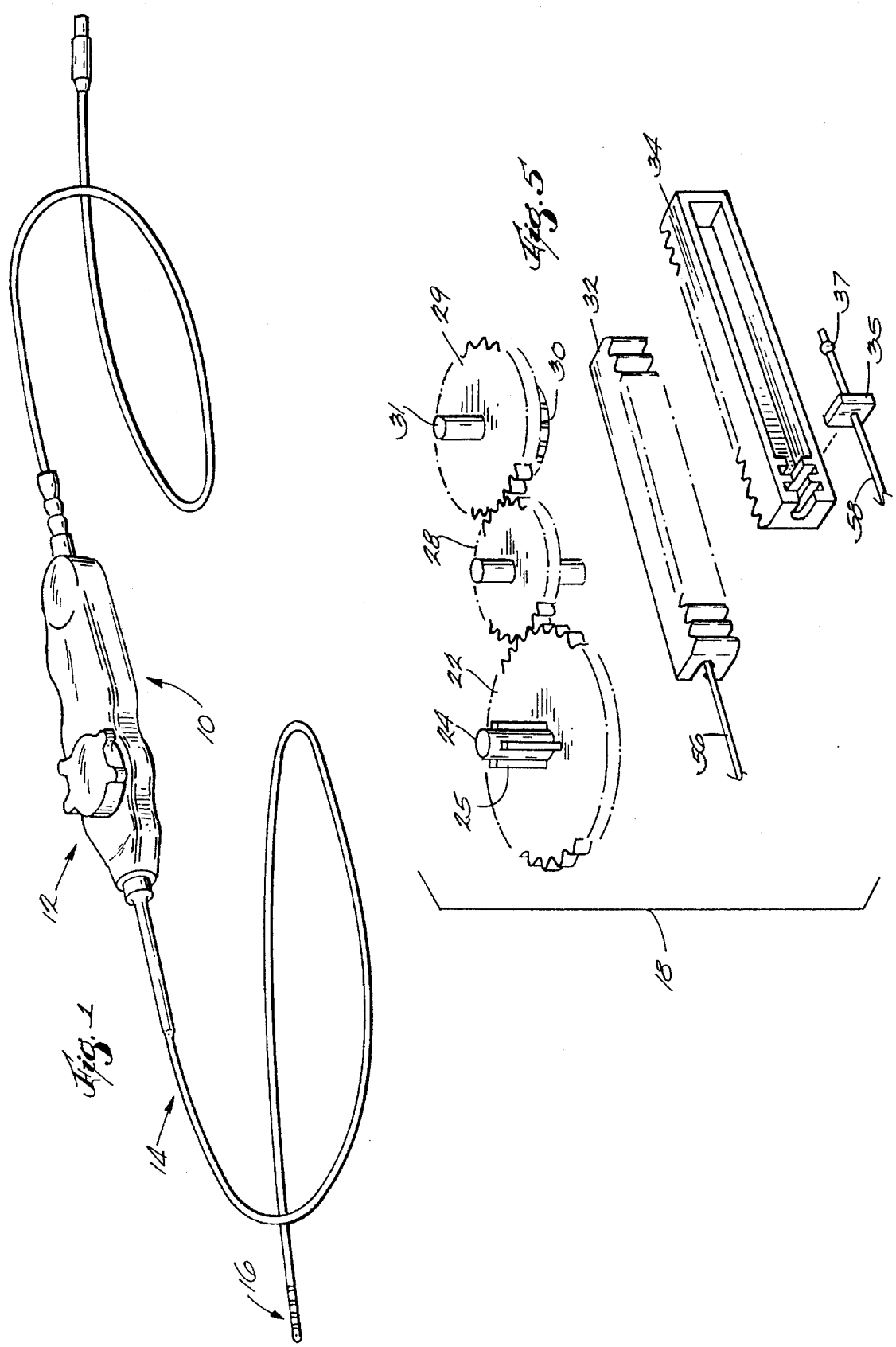

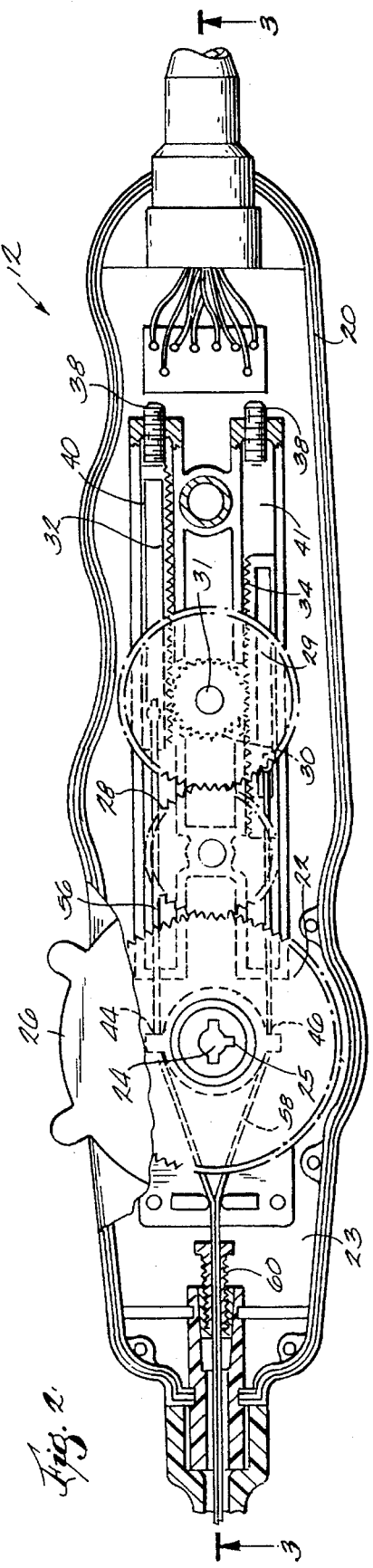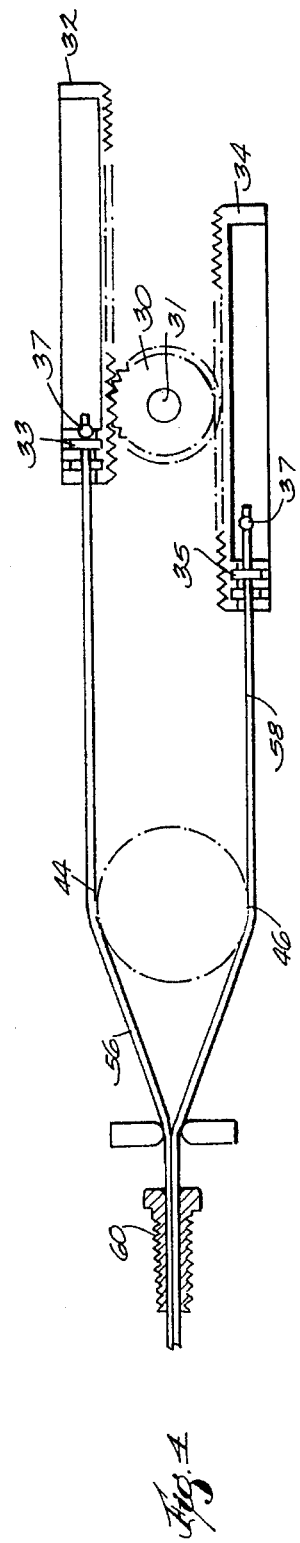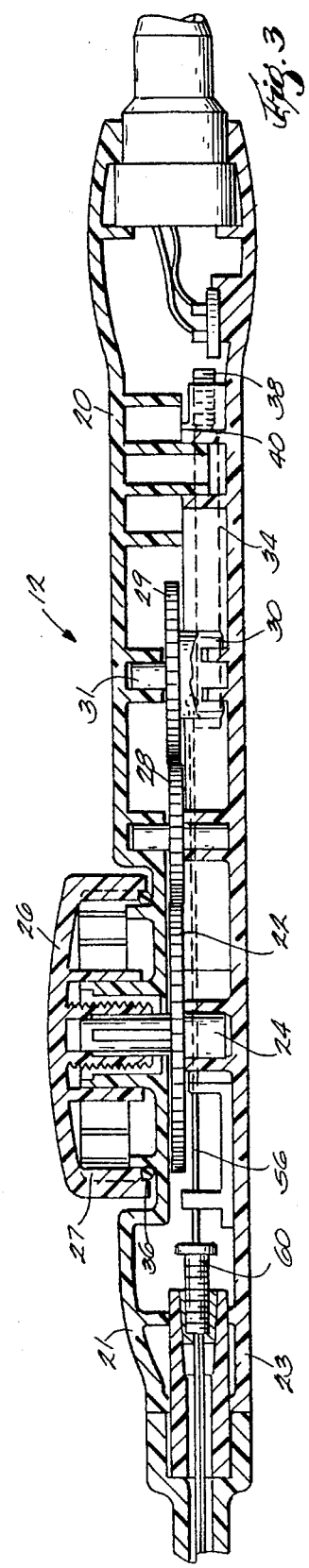

CATHETER STEERING MECHANISM

This is a continuation of application Ser. No. 07/976,693 filed on Nov. 13, 1992 now U.S. Pat. No. 5,364,351.

FIELD OF THE INVENTION

The invention generally relates to catheters. In a more specific sense, the invention relates to improved steering mechanisms for catheters that can be steered and manipulated within interior regions of the body from a location outside the body.

BACKGROUND OF THE INVENTION

Physicians make widespread use of catheters today in medical procedures to gain access into interior regions of the body. In its important that the physician can control carefully and precisely the movement of the catheter within the body.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery (typically the femoral artery) into the interior region of the heart that is to be treated. The physician then further manipulates a steering mechanism to place the electrode carried on the tip of the catheter into direct contact with the tissue that is to be ablated. The physician directs radio frequency energy into the electrode tip to ablate the tissue and form a lesion.

Cardiac ablation especially requires the ability to precisely bend and shape the tip end of the catheter to position the ablation electrode. Previous steering control mechanism have generally applied pulling and pushing forces on a pair of steering wires by winding and unwinding them around a rotatable cam wheel. Such mechanisms have a relatively short life due to metal fatigue occurring in the wires caused by repeated bending and straightening thereof.

SUMMARY OF THE INVENTION

The invention provides an improved steering device for manipulating the distal end of a catheter by simultaneously pulling on one of a pair of control wires while not applying tension on the other one of said pair. An important aspect of the invention relates to providing a steering control mechanism that moves the steering wires by applying linear rather than rotary forces on the wires. A related aspect involves minimization of compressive or buckling forces on the wires while applying tension thereto to steer the catheter tip assembly.

Briefly summarized, the invention provides an improved catheter steering mechanism for retracting a first catheter steering wire by applying tension to it while simultaneously allowing a second catheter steering wire to remain static, or at rest and vice versa. The mechanism includes at least one rotatable gear and means, such as a rotatable knob, for manually rotating the gear. A first linearly slidable toothed rack is attached to the proximal end of one steering wire, and a second linearly slidable toothed rack is attached to the proximal end of the other steering wire. A toothed gear rotatable by rotation of the knob engages each of the toothed racks to move them linearly in opposite directions in response to rotation of said gear. Preferably three intermeshing gears are used so that movements of the racks are in the same direction as the rotation of the knob. Preferably the steering wires are connected to the racks by connections that transfer tension as the racks move away from the wires but allow the wires to be slack when the rack moves toward its associated wire.

In accordance with another aspect of the invention, the knob frictionally engages a housing wherein it is contained so that the wires remain in a selected orientation until moved by further rotation of the knob. Further aspects will be apparent from the following detailed description and accompanying drawings.

BRIEF DESCRIPTION OF THE DRAWINGS

FIG. 1 is a perspective view of a catheter that embodies the features of the invention;

FIG. 2 is a top section view of the catheter with fragmentary parts included for illustrative purposes;

FIG. 3 is a side elevational view taken along Line 3—3 of FIG. 2;

FIG. 4 is a top view of the reciprocal racks and guide wire assembly of the catheter; and FIG. 5 is an exploded view of the drive gear assembly and reciprocal racks for the catheter.

DESCRIPTION OF THE PREFERRED EMBODIMENTS

FIG. 1 shows the assembly of a steerable catheter 10 that embodies the features of the invention. As there shown, the catheter 10 includes three main parts or assemblies: the handle assembly 12, the guide tube assembly 14, and the electrode tip assembly 16.

The catheter 10 can be used in many different environments. This specification will describe the catheter 10 as used to provide electrophysiologic therapy in the interior regions of the heart.

When used for this purpose, a physician grips the handle assembly 12 to steer the guide tube assembly 14 through a main vein or artery, such as the femoral artery, into the interior region of the heart that is to be treated. The physician then further manipulates a steering mechanism 18 on the handle assembly 12 (which will be described later) to place the electrode tip assembly 16 in contact with the tissue that is to be ablated. The physician directs radio frequency energy into the electrode tip assembly 16 to ablate the tissue contacting the electrode tip assembly 16.

As FIGS. 2 and 3 best show, the handle assembly 12 includes a housing 20 that encloses the steering mechanism 18. The steering mechanism 18 includes a rotating toothed gear 22 carried on a shaft 24 within the housing 20. The toothed gear 22 and control knob 26 are attached to shaft 24 by splines 25. Toothed gear 22 is seated for rotation between the upper part 21 and lower part 23 of housing 20. The control knob 26 seats against an O-ring 36, which seals the housing and also provides resistance against movement so that the catheter tip 16 will remain in a selected curved position until a new position is selected by the physician. Internal ribs 27 within knob 26 serve as surfaces for knob 26 to retain O-ring 36.

Movement of the control knob 26 by the user rotates the toothed gear 22 and shaft 24 within the upper housing 21 and the lower housing 23. Clockwise movement of the control knob 26 rotates the toothed gear 22 clockwise, meshed intermediate gear 28 counterclockwise and gear 29 clockwise. Gears 29 and 30 are mounted for rotation together on shaft 31. Linearly reciprocating racks 32 and 34 are both provided with teeth that intermesh with those on gear 30. Thus the clockwise movement of control knob 26 moves rack 32 to the left as viewed in FIG. 2 and rack 34 to the right. Counterclockwise movement of the control knob 26 reverses the direction of each of these movements. Set screws 38 at the ends of tracks 40 and 41, within which racks 32 and 34, respectively, are slidably contained, physically limits the range of rearward movement of racks 32 and 34 within the lower housing 23. The limit of movement of catheter tip 16 is thus adjustable.

The steering wires 56 and 58 extend from the respective ends of the racks 32 and 34 along the associated left and right side bearing surfaces 44 and 46 in lower housing shell 23. The steering wires 56 and 58 exit the front of the upper housing 21 and the lower housing 23 through the interior bore of a tension screw assembly 60.

The distal ends of the steering wires 56 and 58 are attached to the electrode tip assembly 16. They extend from the racks 32 and 34 through the guide tube assembly 14 to the electrode tip assembly 16. The use of reciprocating racks 32 and 34 minimizes the amount of bending of the control wires 56 and 58 during reciprocation and thus minimizes stress failure of wires.

The use of the rack and pinion gears in connection with the present invention enables the rotating motions applied to knob 26 to be converted into linear reciprocating motion of the steering wires 56 and 58 attached to the electrode tip assembly 16.

By rotating the toothed gear 22 to the left (by moving the control knob 26 counterclockwise), the left rack 34 applies tension to control wire 58 to impose a discrete, constant pulling force that causes the electrode tip assembly 16 to bend to the left. Tension is applied to wire 58 through retainer 35 and wire termination 37 while retainer 33 allows wire 56 to be slack and thus moved only by tension transferred through the catheter.

Also, by rotating the toothed gear 22 to the right (by moving the control knob 26 clockwise), the right steering wire 56 is pulled by rack 32 while wire 58 is allowed to remain static, as seen in FIG. 4. The tension imposes a discrete, constant pulling force that causes the electrode tip assembly 16 to bend to the right.

The component parts of the handle assembly 12 can be constructed of various materials, depending upon the durability needed and the sterilization process used.

For example, when EtO sterilization is used, the housing 20, control knob 26 and gear shaft 24 can be made of a polycarbonate material. In this arrangement, the toothed gears 22, 28, 29, and 30 can be made of an acetal material. These plastic materials are durable and EtO sterilizable. In this assembly, the tension screw 60, guide wires 56, 58, wire retainers 33, 35, wire termination 37 and electrical connectors are preferably made of a metallic material such as brass or stainless steel. The guide tube assembly 14 can be made in various lengths. In the illustrated, the guide tube assembly 14 is about 100 cm in length. Various other details of the catheter assembly are known to those skilled in the art and do not form a part of the present invention.

We claim:

1. A catheter steering mechanism for retracting a catheter steering wire to bend a catheter distal tip comprising:

a rotatable gear;

means for manually rotating said gear;

at least one linearly slidable toothed rack attached to the proximal end of said steering wire, and a toothed gear rotatable by engaging said manual rotating means engaging said toothed rack to move said rack linearly in opposite directions in response to rotation of said gear, thereby applying tension to said wire.

2. A mechanism according to claim 1, wherein said toothed gear is driven by a series of intermeshing gears that are rotated by said manual means for rotation.

3. A mechanism according to claim 1 wherein said steering wire is connected to said rack by means that transfers tension as said rack move away from said wire but allows said wire to be slack when said rack moves toward said wire.

4. A mechanism according to claim 1 wherein said means for manually rotating said gear is a manually rotatable knob.

5. A mechanism according to claim 4 wherein said mechanism is contained in a housing and said knob frictionally engages said housing whereby the wire remains in a selected orientation until moved by further rotation of said knob.

6. A cardiac probe comprising a catheter having at least one electrode at the distal end thereof and at lest one steering wire extending through said catheter from the distal end to the proximal end thereof, the proximal end of said catheter being attached to a handle that houses a steering mechanism for said wire, said steering mechanism comprising a manually rotatable knob connected for rotation together with a first rotatable gear;

said rotatable gear being intermeshed with a second rotatable gear;

said second rotatable gear being intermeshed with a third rotatable gear that is connected for rotation together with a pinion gear;

said pinion gear being intermeshed with a linearly movable toothed rack slidably contained in a track within said housing;

the proximal end of said guide wire being connected to said toothed rack;

said wire being connected to an end of said toothed rack by means of a floating connection with enables movement of the rack to apply tension to said steering wire but which allows said wire remain slack when said rack is moved toward said wire; and means for frictional engagement between said knob and said housing whereby the tip of said catheter will remain in a selected orientation.

* * * * *

UNITED STATES PATENT AND TRADEMARK OFFICE
CERTIFICATE OF CORRECTION

PATENT NO.    :  5,456,664

DATED         :  October 10, 1995

INVENTOR(S)   :  Heinzelman et al.

It is certified that error appears in the above-identified patent and that said Letters Patent is hereby corrected as shown below:

Column 4, Line 20    Delete "move" and insert — moves —
Column 4, Line 29    Delete "lest" and insert — least —
Column 4, Line 49    Delete "with" and insert — which —
Column 4, Line 51    Insert — to — between "wire" and "remain"

Signed and Sealed this

Twentieth Day of August, 1996

Attest:

BRUCE LEHMAN

Attesting Officer                    *Commissioner of Patents and Trademarks*